(12) United States Patent
Bogart et al.

(10) Patent No.: US 7,415,858 B2
(45) Date of Patent: Aug. 26, 2008

(54) GRINDLESS SURGICAL NEEDLE MANUFACTURE

(75) Inventors: Michael W. Bogart, Milford, CT (US); Andrew J. Vacco, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 114 days.

(21) Appl. No.: 11/358,195

(22) Filed: Feb. 21, 2006

(65) Prior Publication Data

US 2007/0193326 A1    Aug. 23, 2007

(51) Int. Cl.
*B21G 1/00* (2006.01)
*A61B 17/06* (2006.01)

(52) U.S. Cl. .............................. 72/340; 163/5; 606/223

(58) Field of Classification Search ................ 72/341, 72/340, 377; 163/1, 5; 606/223
See application file for complete search history.

(56) References Cited

U.S. PATENT DOCUMENTS

| | | | |
|---|---|---|---|
| 3,038,475 A * | 6/1962 | Orcutt .................... 606/223 |
| 4,672,734 A | 6/1987 | Kawada et al. |
| 4,785,868 A | 11/1988 | Koenig, Jr. |
| 4,799,484 A | 1/1989 | Smith et al. |
| 4,805,292 A | 2/1989 | Noguchi |
| 4,905,695 A | 3/1990 | Bendel et al. |
| 4,932,961 A | 6/1990 | Wong et al. |
| 4,959,068 A | 9/1990 | Bendel et al. |
| 4,968,362 A | 11/1990 | Prasad |
| 5,002,564 A | 3/1991 | McGregor et al. |
| 5,002,565 A | 3/1991 | McGregor |
| 5,030,228 A | 7/1991 | Wong et al. |
| 5,057,401 A | 10/1991 | Borysko et al. |
| 5,100,431 A | 3/1992 | Buster et al. |
| 5,100,432 A | 3/1992 | Matsutani |
| 5,123,910 A | 6/1992 | McIntosh |
| 5,155,943 A | 10/1992 | Matsutani et al. |
| 5,178,628 A | 1/1993 | Otsuka et al. |
| 5,217,586 A | 6/1993 | Datta et al. |
| 5,231,771 A | 8/1993 | Samsel |
| 5,258,013 A | 11/1993 | Granger et al. |
| 5,263,974 A | 11/1993 | Matsutani et al. |
| 5,298,115 A | 3/1994 | Leonard |
| 5,330,441 A | 7/1994 | Prasad et al. |
| 5,342,397 A | 8/1994 | Guido |
| 5,411,613 A | 5/1995 | Rizk et al. |

(Continued)

FOREIGN PATENT DOCUMENTS

EP        0 650 698 A1       5/1995

(Continued)

OTHER PUBLICATIONS

European Search Report for EP 07003237.0 date of completion is May 16, 2007 (8 pages).

*Primary Examiner*—Daniel C Crane (57) ABSTRACT

Surgical needles are produced by immersing a needle possessing a distal end surrounded at least in part by flash material and a body portion in an acid bath according to a predetermined sequence, wherein the distal end of the needle is exposed to the acid bath under conditions sufficient to remove flash material from the distal end of the needle and the body portion of the needle is exposed to the acid bath under conditions sufficient to provide a matte finish on at least a portion of the body portion of the needle.

21 Claims, 4 Drawing Sheets

U.S. PATENT DOCUMENTS

| | | |
|---|---|---|
| 5,415,707 A | 5/1995 | Bendel et al. |
| 5,464,422 A | 11/1995 | Silverman |
| 5,476,480 A | 12/1995 | Matsutani et al. |
| 5,477,604 A | 12/1995 | Smith et al. |
| 5,527,340 A * | 6/1996 | Vogel .................... 606/205 |
| 5,533,982 A | 7/1996 | Rizk et al. |
| 5,539,973 A | 7/1996 | Smith et al. |
| 5,622,636 A | 4/1997 | Huh et al. |
| 5,626,043 A | 5/1997 | Bogart et al. |
| 5,630,268 A | 5/1997 | Smith et al. |
| 5,644,834 A | 7/1997 | Smith et al. |
| 5,649,961 A | 7/1997 | McGregor et al. |
| 5,661,893 A | 9/1997 | Smith et al. |
| 5,683,416 A | 11/1997 | McGregor et al. |
| 5,693,454 A | 12/1997 | Munoz |
| 5,730,732 A | 3/1998 | Sardelis et al. |
| 5,749,897 A | 5/1998 | Matsutani et al. |
| 5,762,811 A | 6/1998 | Munoz |
| 5,776,268 A | 7/1998 | McJames et al. |
| 5,783,001 A | 7/1998 | Sardelis et al. |
| 5,797,961 A | 8/1998 | Smith et al. |
| 5,800,666 A | 9/1998 | Bonham, Jr. et al. |
| 5,814,166 A | 9/1998 | Ackerman et al. |
| 5,853,423 A | 12/1998 | McGregor et al. |
| 5,897,572 A | 4/1999 | Schulsinger et al. |
| 5,913,875 A | 6/1999 | Smith et al. |
| 5,928,207 A | 7/1999 | Pisano et al. |
| 5,935,411 A * | 8/1999 | Brown et al. ................ 205/672 |
| 6,018,860 A | 2/2000 | Smith et al. |
| 6,214,030 B1 | 4/2001 | Matsutani et al. |
| 6,280,647 B1 | 8/2001 | Muramatsu et al. |
| 6,322,581 B1 | 11/2001 | Fukuda et al. |
| 6,406,638 B1 | 6/2002 | Stoeber et al. |
| 6,432,295 B1 | 8/2002 | Szameitat et al. |
| 6,447,664 B1 | 9/2002 | Taskovics et al. |
| 6,497,994 B1 | 12/2002 | Kafrawy |
| 6,503,231 B1 | 1/2003 | Prausnitz et al. |
| 6,527,938 B2 | 3/2003 | Bales et al. |
| 6,767,341 B2 | 7/2004 | Cho |
| 6,936,297 B2 | 8/2005 | Roby et al. |
| 2004/0106948 A1* | 6/2004 | Cunningham ............... 606/223 |
| 2005/0044922 A1 | 3/2005 | Bogart |
| 2005/0222617 A1 | 10/2005 | Ororz, Jr. |

FOREIGN PATENT DOCUMENTS

| | | |
|---|---|---|
| EP | 1 506 743 A | 2/2005 |

* cited by examiner

GRINDLESS SURGICAL NEEDLE MANUFACTURE

BACKGROUND

1. Technical Field

The present disclosure relates to needle manufacturing processes and needles produced thereby. More specifically, grindless methods for producing cutting edge needles are described as are cutting edge needles produced thereby.

2. Background of Related Art

Suturing needles having cutting edges are generally known in the art. Cutting edge needles generally include a suture attachment portion at one end of the needle, a body portion, and a pointed tip portion containing the cutting edges at the other end of the needle. Typically, cutting edge needles are manufactured by subjecting a needle blank to various metal working operations such as cutting, pressing, coining, trimming and the like. See, for example, U.S. Pat. No. 5,776,268 and U.S. Pat. No. 5,749,897, the entire disclosures of which are incorporated herein by this reference.

There remains room for improvement in the art of cutting edge needle manufacture.

SUMMARY

Methods for manufacturing surgical needles in accordance with the present disclosure can be entirely devoid of any grinding process. In embodiments, the methods for manufacturing surgical needles include pressing a needle blank to define a needle possessing a generally tapered end portion surrounded at least in part by flash material, and immersing the needle in an acid bath according to a predetermined sequence wherein the generally tapered end portion is exposed to the acid bath under conditions sufficient to remove flash material from the generally tapered end portion and the body of the needle is exposed to the acid bath under conditions sufficient to provide a matte finish on the body of the needle.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiment(s) of the process for manufacturing a surgical needle of the present disclosure will now be described in detail with reference to the drawings wherein like reference numerals identify similar or like elements throughout the several views. As used herein, the term "proximal" refers to that portion of the surgical needle having a suture mounting structure, while the term "distal" refers to that portion of the surgical needle having a tip designed to penetrate tissue.

Figure 1:
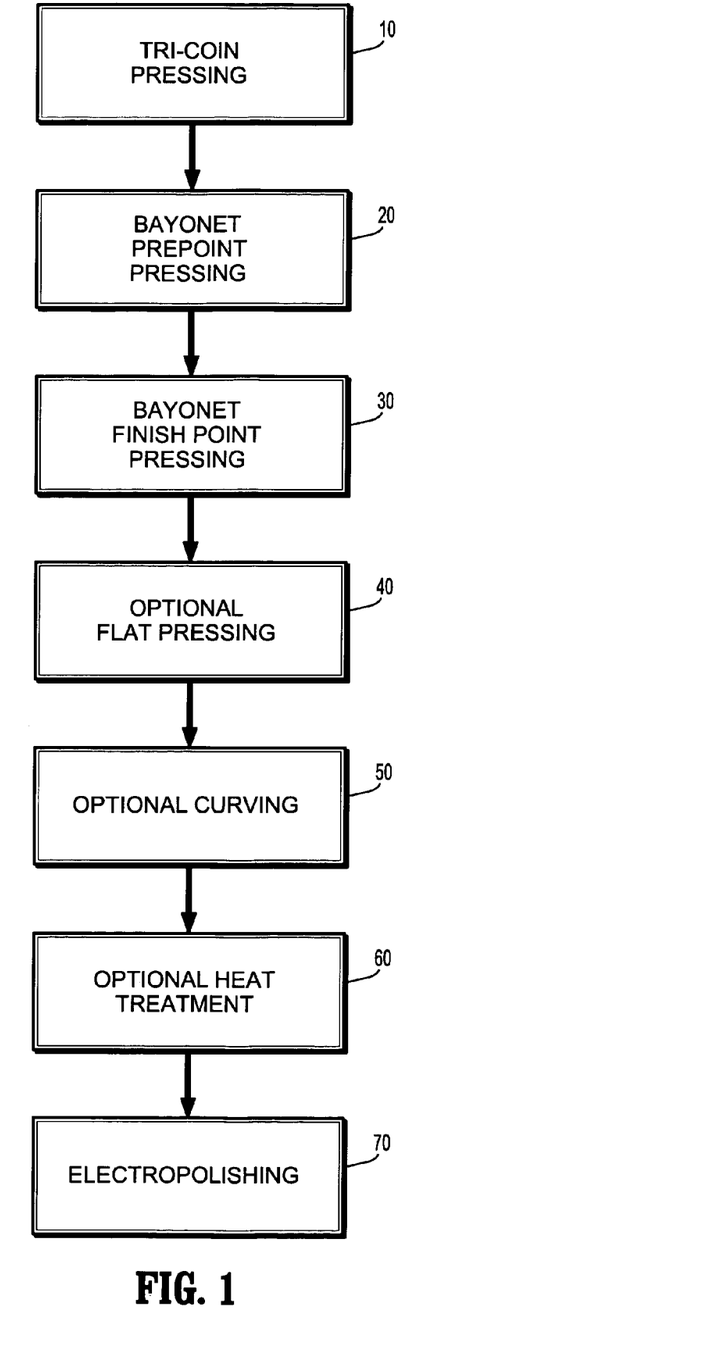
FIG. 1 is a block diagram of an embodiment of a process of manufacturing a surgical needle in accordance with the principles of the present disclosure.

Referring now to the block diagram of FIG. 1, there is illustrated a method for needle manufacture in accordance with the principles of the present disclosure. A needle blank in the form of a cylindrical rod having a desired or predetermined length is provided. The needle blank is to be eventually formed into a surgical needle. The needle blank may be cut from suitable stock, including stainless steel, titanium or titanium alloys. The needle blank may also have a drilled recess in the proximal end for receiving a surgical suture to attach a suture to the needle. It is also contemplated that the needle stock may have an open channel, an eye, etc. formed at the proximal end thereof for receiving and attaching the suture as is known in the art. In embodiments, the needle blank may be produced from a precipitation hardened maretensitic stainless steel alloy obtained as wire needle stock ranging from about 0.004" to about 0.025" and, in embodiments, from about 0.012" to about 0.021" in diameter. One suitable precipitation hardened maretensitic stainless steel alloy is Bioline 1RK91, commercially available from Sandvik Materials Technology, Summit, Pa.

Figure 2A:
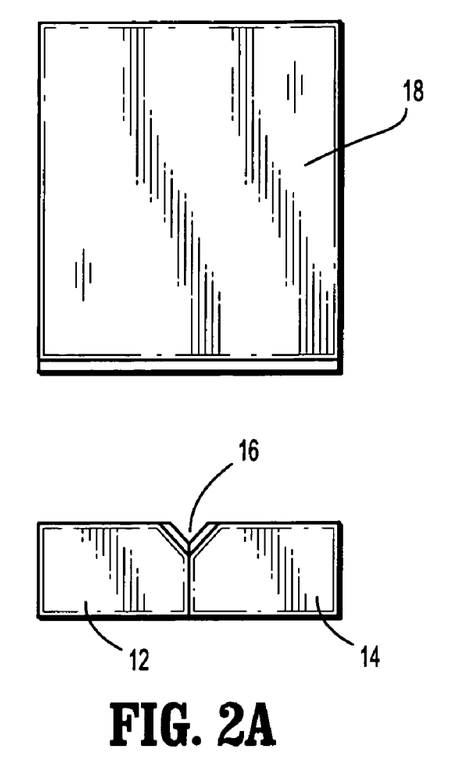
FIG. 2A is a side plan view of the dies utilized in the tri-coin pressing operation.

With reference to FIGS. 1 and 2A, the first operation is a pressing operation, such as, for example, tri-coin pressing operation 10. Tri-coin pressing operation 10 imparts a substantially triangular cross-sectional configuration to at least a portion of the distal end of the needle blank and, in embodiments to a majority of the length of the needle blank. Tri-coin pressing operation 10 is achieved using a tri-coin press that incorporates a die mechanism having two lower dies to form a cavity. As set forth in FIG. 2A, the lower dies 12 and 14 include inclined planar coining surfaces defining a concavity or recess 16 within the lower dies 12 and 14 for receiving the distal end of the needle blank. The distal end of the needle blank may be positioned within the recess 16 and the die mechanism is activated whereby the upper planar die 18 engages and coins the distal end of the needle blank. The dies 12, 14 and 18 may be formed of a carbide material although other materials are envisioned as well. In FIG. 2A, the dies 12 and 14 are shown approximated together, but open with respect to planar die 18.

Figure 2B:
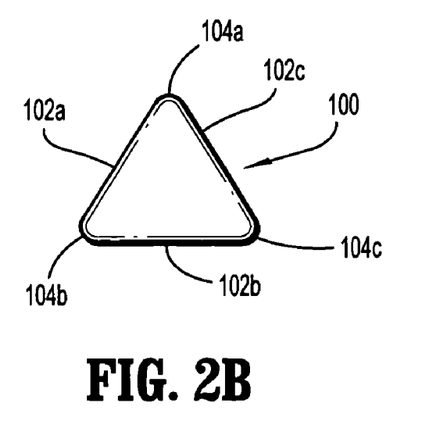
FIG. 2B is an end view of the needle subsequent to the tri-coin pressing operation.

The resulting coined needle blank has a distal end portion with a cross-section generally defining a three-sided equilateral triangle. An end-on view of the distal end of needle blank 100 after tri-coin pressing operation 10 is depicted in FIG. 2B showing three planar surfaces 102a, 102b and 102c and three rounded corners 104a, 104b and 104c.

Figure 3A:
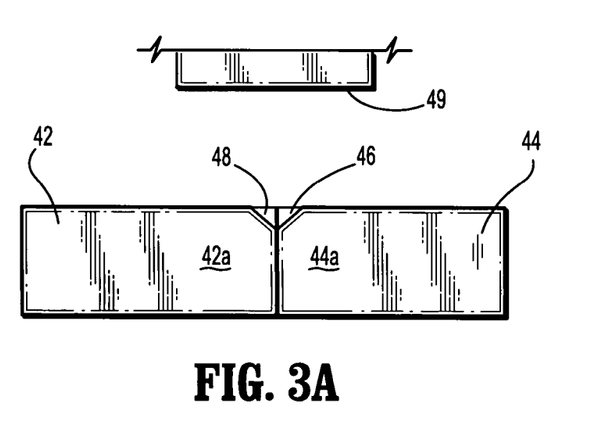
FIG. 3A is a plan view of a pair of dies utilized in the bayonet form operation.
Figure 3B:
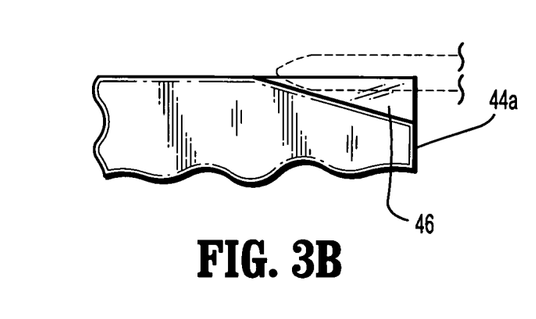
FIG. 3B is a plan view illustrating the angled cut of the dies of FIG. 3A.

With reference again to FIG. 1, the next step in the process is bayonet prepoint pressing operation 20. Bayonet prepoint pressing operation 20 is achieved using a press that incorporates two lower dies and an upper punch (collectively "bayonet dies") formed to define a cavity. With reference to FIG. 3A, the lower dies, i.e., left and right dies 42, 44 each include an angled or sloped cut 46 in their upper surfaces which when joined together define a general bayonet-shaped or triangular-shaped recess 48 decreasing in cross-section from the front surface 42a, 44a of the dies to the middle die area. FIG. 3B is a plan view illustrating the angled cut of the dies of 42 and 44 of FIG. 3A. The press further includes an upper punch 49 which moves to engage at least a portion of the distal end of coined needle blank 100. In operation, a portion of the distal end of coined needle blank 100 is placed within the triangular-shaped recess 48 of the left and right dies 42, 44. The press is operated such that the upper punch 49 advances to engage a portion of the distal end of coined needle blank 100 thereby pressing the distal end of the needle blank into a truncated, generally bayonet shape. This coining causes the needle material to flow within the recess and creates some overflow flash on each side edge of the distal end of the needle blank.

With reference again to FIG. 1, the next step in the process is bayonet finish point pressing operation 30. Bayonet finish point pressing operation 30 continues to reshape the distal end of the needle blank and may be achieved using a press that incorporates the same dies described above in connection with bayonet prepoint pressing operation 20 (i.e., the die mechanism depicted in FIG. 3A). The difference in the needle configuration resulting from the finish point press, as compared to the prepoint press step, is obtained by inserting the distal end of the needle blank further into the die mechanism.

Figure 3C:
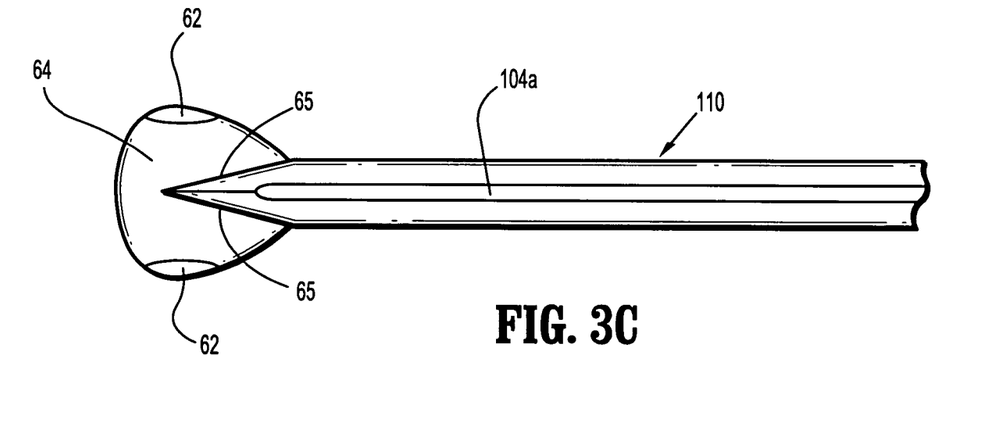
FIG. 3C is a plan view of the needle end subsequent to the bayonet form operation.

Subsequent to bayonet finish point pressing operation 30, the pointed configuration of the distal end of the needle is substantially defined; however, a substantial amount of flash may be present adjacent the portion of the distal end of the needle blank that has been subjected to bayonet prepoint pressing operation 20 and bayonet finish point pressing operation 30. For example, overflow flash 62 from the bayonet prepoint pressing operation 20 and overflow flash 64 from bayonet finish point pressing operation 30 may impart a winged appearance to the distal end of the needle blank as shown in FIG. 3C. For convenience, the needle blank that has been subjected to bayonet prepoint pressing operation 20 and bayonet finish point pressing operation 30 will be referred to hereinafter as the flash-bearing needle 110. As those skilled in the art will appreciate, flash may result from needle material overflow at a location adjacent triangular recessed area 48. The flash may extend outwardly from the normal perimeter 65 that will form the cutting edges 58 at the distal end of the needle upon further processing. The thinner the flash, the more readily it can be removed by further processing. Typically, the thickness of the flash may be from about 0.001 inches to about 0.004 inches, and in embodiments, from about 0.001 inches to about 0.002 inches thick.

Figure 4:
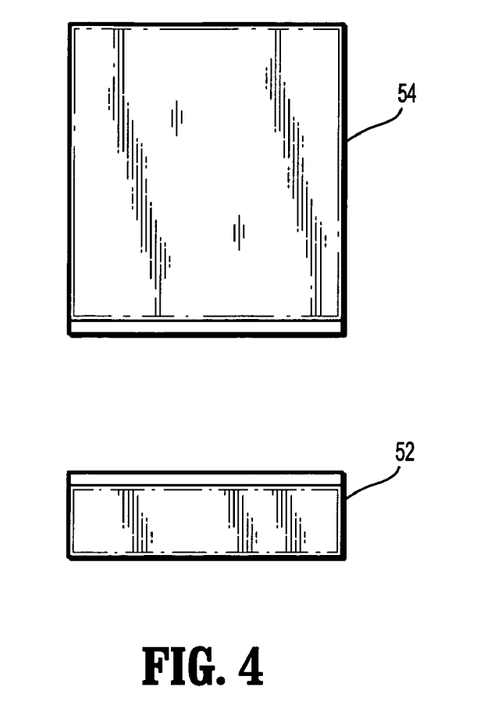
FIG. 4 is a side plan view of a pair of dies utilized in an optional flat press operation.

With reference to FIG. 1, the next step in the operation is optional flat pressing operation 40 of the flash-bearing needle 110. Flat pressing operation 40 may be utilized to impart a four sided configuration (i.e., a generally trapezoidal shape) to at least a central portion of flash-bearing needle 110 between the tapered distal end and the proximal, suture attachment end. As depicted in FIG. 4, the flat press includes upper punch 54 and lower die 52. Upper punch 54 and lower die 52 may be formed of a carbide material although other materials are envisioned as well. Upper punch 54 has a flat pressing surface and lower die 52 includes a flat pressing surface. A central portion of the flash-bearing needle 110 is positioned between upper punch 54 and lower die 52. Upper punch 54 is then activated to engage the central portion of the flash-bearing needle 110 to impart a generally trapezoidal configuration thereto. If desired, an inclination may be incorporated into upper punch 54 to provide a tapered, generally trapezoidal configuration to the central portion of the flash-bearing needle 110. Selection of a suitable angle of inclination is within the purview of those skilled in the art. Typically, inclinations of less than 5° may be imparted to upper punch 54 and, in embodiments, an inclination of less than 2° may be used. When used, the taper should decrease distally.

The next operation is an optional curving operation 50 to curve flash-bearing needle 110. Optional curving operation 50 may be performed by any suitable apparatus. One suitable curving apparatus is described in commonly assigned U.S. Pat. No. 5,626,043, the entire disclosure of which is hereby incorporated by reference herein. Other suitable curving methods and machines will be readily apparent to those skilled in the art. As those skilled in the art will appreciate, because curving operation 50 is optional, methods in accordance with the present disclosure may be used to form straight needles.

It is also contemplated that a heat treatment 60 optionally may be employed to enhance the mechanical properties of the needle ultimately produced by the process described herein. Optional heat treatment 60 can be performed on flash-bearing needle 110 before removal of overflow flash 62, 64. In embodiments, flash-bearing needle 110 may be placed in a foil pouch which, in turn, may be placed on an oven rack in a furnace. The furnace door is closed and a vacuum may be applied. When the desired reduced pressure is achieved (e.g., about $0.1 \times 10^{-2}$ atm. or below), the furnace is set to a desired temperature from about 250° C. to about 600° C., in embodiments from about 300° C. to about 500° C., for a period of time from about 3 hours to about 5 hours, in embodiments from about 3.5 hours to about 4.5 hours. After heating, the chamber may be filled with an inert gas, such as nitrogen gas, and the foil pouches may then be removed from the furnace chamber.

The flash-bearing needle 110 may then be subjected to electropolishing process 70 (see FIG. 1) by submerging the flash-bearing needle 110 in an acid bath. Electropolishing process 70 removes the excess flash material (created by the bayonet prepoint and finish point press process steps described above) from the distal end of flash-bearing needle 110 and sharpens the cutting edges 58 and the needle point. In addition to removing the flash adjacent the distal end of flash-bearing needle 110, electropolishing process 70 removes any additional marks, such as annealing marks, left by any other prior treatments to which flash-bearing needle 110 has been subjected. In embodiments, electropolishing process 70 can advantageously produce a matte-like finish on the needle ultimately produced by the methods described herein, to facilitate retention of any subsequent coating which may be applied to the needle.

The electropolishing process may utilize any acid solution suitable for use with surgical needles and similar devices, including, but not limited to, solutions containing phosphoric acid, sulfuric acid, glycolic acid and combinations thereof, optionally in combination with water or alcohols, including ethylene glycols. In embodiments, a mixture containing from about 30% to about 70% by weight phosphoric acid and from about 70% to about 30% by weight sulfuric acid may be used as the acid bath. The acid bath may be temperature controlled, to a temperature of from about 80° F. to about 200° F., in embodiments from about 90° F. to about 110° F., to produce a matte surface finish. The temperature may be adjusted to alter the rate of stock removal; the higher the temperature, the more aggressive the rate of stock removal.

In embodiments, electropolishing process 70 may include immersing one or more flash-bearing needles in a tank containing the acid bath followed by rinsing with water. The number of rinses with water may vary from about 1 to about 10, in embodiments from about 2 to about 6, with about 4 separate rinses with water being used in some embodiments. Electropolishing process 70 may be performed any suitable device, such as, for example, by a computer-controlled, multi-station electropolishing machine.

Flash-bearing needles to be treated with the above-described acid solution may be first placed into a needle fixture capable of holding any number of flash-bearing needles. The needle fixture may orient each needle in the same direction. In embodiments, the proximal end of the flash-bearing needles are loaded into a fixture and the formed distal end of the flash-bearing needles with remaining flash face outward from the fixture. Once the flash-bearing needles are loaded into the needle fixture, the needle fixture may be placed onto the index arm of an electropolisher. The needle fixture, the index arm, or both may, if desired, be partially or entirely plated (e.g., with gold) using know techniques to improve the electrical contact therebetween. Upon commencement of the electropolishing process, the needle fixture may be lowered by the index arm onto a stationary, electrically conductive metal holder, in embodiments an anode, over the tank holding the acid solution so that the flash-bearing needles are vertically oriented generally along their longitudinal axes with their distal ends pointed down. The tank holding the acid solution may, in some embodiments, contain a stationary cathode therein. The acid solution within the bath optionally may be stirred.

Where a computer-controlled electropolishing machine is utilized, the computer utilized with the electropolisher identifies that the fixture has been properly placed on the metal holder and then raises the tank holding the acid solution to determine the zero point position of the needle blanks. The zero point position may be determined by the electrical conductivity at the interface between the distal ends of the flash-bearing needle(s) and the acid solution. The tank holding the acid bath may be raised by any means within the purview of those skilled in the art. In some embodiments, a stepper motor may be utilized to raise the tank holding the acid solution. Such a stepper motor may be attached to the tank holding the acid bath, or the tank holding the acid bath may be placed on a table which, in turn, may be attached to the stepper motor. Once the zero point position has been determined, the tank holding the acid bath may be further elevated to predetermined levels for controlled periods of time while varying voltages are applied to the fixtured needle blanks. A custom immersion and electrical profile may be executed depending upon the size and configuration of the flash-bearing needles being processed and the ultimate needle configuration to be produced.

The distal ends of the flash-bearing needles, which are the first portion to be submerged in the acid solution, remain in the acid solution for the longest period of time during treatment. Thus, as will be readily apparent to those skilled in the art, in embodiments the electropolishing process of the present disclosure treats the distal ends of the flash-bearing needles differently from the central and proximal portions of the flash-bearing needles and thus both removes flashing from the distal ends of the flash-bearing needles and provides a desired finish on the remaining portions of the flash-bearing needles that are subjected to the acid bath. As those skilled in the art will appreciate, the acid bath may affect all surfaces of the flash-bearing needles simultaneously.

The specific conditions under which the flash-bearing needles are immersed in the acid bath may vary depending on their size, the amount of material to be removed, and the type of finish (matte or shiny) that is desired on the needle ultimately produced. The amount of time the flash-bearing needles remain immersed in the acid solution can be, for example, from about 60 seconds to about 500 seconds, in embodiments from about 100 seconds to about 300 seconds. In embodiments, the generally distal ends of the flash-bearing needles may remain in the acid bath for a period of time at least about twice as long, and in embodiments as much as about four times as long, as the central portion of the flash-bearing needles remains within the acid bath.

Suitable voltages applied during electropolishing can be up to 30 volts, typically, from about 0.1 volts to about 12 volts, in embodiments from about 1 volt to about 10 volts. The voltage applied during immersion of the flash-bearing needles can change during the electropolish process. For example, the voltage applied when the distal ends of the flash-bearing needles are immersed into the acid bath can be higher than the voltage applied when the central portion of the flash-bearing needles are immersed in the acid bath. In embodiments, the voltage applied when at least a portion of the distal ends of the flash-bearing needles is immersed into the acid bath is at least twice as much as the voltage applied when at least a portion of the central portion of the flash-bearing needles is immersed in the acid bath.

By controlling the rate of immersion, the flash-bearing needles may be submerged in the acid solution at varying depths for predetermined varying periods of time. Those skilled in the art will readily envision suitable immersion conditions for achieving desired results on specific needles.

In embodiments, a process in accordance with this disclosure involves immersing the flash-bearing needles in an acid bath according to a predetermined sequence wherein the distal ends of the flash-bearing needles are exposed to the acid bath under conditions sufficient to remove flash material from the distal ends of the flash-bearing needles and the central portion of the flash-bearing needles are exposed to the acid bath under conditions sufficient to provide a matte finish on at least the body of the needle. A sample program for the controlled immersion of flash-bearing needles in an acid bath in accordance with the present disclosure is provided below in Table 1:

TABLE 1

Illustrative Electropolishing Program for a .021" × 0.522" Needle

| LINE # | DEPTH (in inches) | TIME (in seconds) | VOLTAGE (in volts) |
|---|---|---|---|
| 1 | 0.075 | 10 | 10.0 |
| 2 | 0.080 | 10 | 9.5 |
| 3 | 0.085 | 10 | 8.5 |
| 4 | 0.090 | 10 | 8.0 |
| 5 | 0.095 | 10 | 7.0 |
| 6 | 0.100 | 10 | 7.0 |
| 7 | 0.105 | 10 | 6.0 |
| 8 | 0.110 | 10 | 5.0 |
| 9 | 0.115 | 10 | 4.5 |
| 10 | 0.120 | 10 | 4.5 |
| 11 | 0.150 | 10 | 4.5 |
| 12 | 0.175 | 5 | 4.5 |
| 13 | 0.200 | 5 | 4.5 |
| 14 | 0.250 | 5 | 4.5 |
| 15 | 0.300 | 5 | 4.0 |
| 16 | 0.350 | 5 | 4.0 |
| 17 | 0.400 | 5 | 4.0 |
| 18 | 0.425 | 5 | 4.0 |
| 19 | 0.0000 | 0 | 0 |
| Total Time | | 145 seconds | |

Upon completion of the desired immersion/electrical profile, the stepper motor controlled tank containing the acid bath may be returned to its zero point reference. Upon returning to the zero point, the fixture contains needles having the desired configuration. The treatment in an acid bath may produce a matte-like finish on the needle. The matte finish facilitates retention of any subsequent coating which may be applied to the needle.

The index arm of the electropolisher then lifts the needle fixture from the anode and will index to the next position over a rinse tank for rinsing with cold water. As noted above, in some embodiments a series of four (4) rinse tanks may be utilized. In embodiments, the rinse tanks may be located on the same table as the tank possessing the acid solution. The fixtured needles are introduced into the first rinse tank by lowering the rotary indexing arm. Process water may be sprayed through a manifold to rinse the needles for varying periods of time. In embodiments, the process water may be sprayed through a manifold to rinse the needles for a period of time corresponding to the total time the needles were immersed in the acid bath. The rotary indexing arm may then be raised, thereby removing the needles from the first rinse tank.

The index arm of the electropolisher will then consecutively index to a position over the next rinse tank and this process may be repeated for second, third, fourth, etc. rinses. The fixtured needles are introduced into each additional rinse tank by lowering the rotary indexing arm, and upon being lowered into each successive rinse tank, the fixtured needles may be sprayed with water for varying periods of time, in embodiments for a period of time corresponding to the total time that the needles were immersed in the acid bath.

Upon completion of the rinse cycle, in embodiments four rinses, the electropolisher may then move the fixture with the needles to any successive steps in the manufacturing process. Additional steps may include drying and the like. In embodiments, the needles may be subjected to a drying step by lowering the fixtured needles into a cavity which permits the flow of hot air to dry the needles. The hot air may be provided in any suitable manner, such as, for example, by a commercial air dryer mounted in a protected enclosure. The temperature may be controlled utilizing a desired potentiometer setting. The needles may be subjected to the hot air for a desired period of time to allow the needle body and barrel to completely dry prior to its removal from the fixture. An example of a suitable method for drying needles of the present disclosure is set forth in U.S. Pat. No. 5,231,771, the entire disclosure of which is hereby incorporated by reference herein.

Once the above process is completed, in embodiments the needles of the present disclosure may be subjected to additional treatments, including coating with any material within the purview of one skilled in the art as suitable for use with a needle. As noted above, in addition to removing flashing from the tips of the needles, the process of the present disclosure may provide a matte finish on the needle surface which may, in embodiments, enhance the adherence of a coating material to the needle. Suitable coating materials include, but are not limited to, silicone materials, PTFE, Teflon, or any similar coatings within the purview of those skilled in the art that enhance the lubricity of the needles and reduce tissue penetration forces found with repeated passing of the needle through tissue. Specific examples of such materials include those disclosed in U.S. Pat. No. 6,936,297, the entire disclosure of which is hereby incorporated by reference herein.

Figure 5:
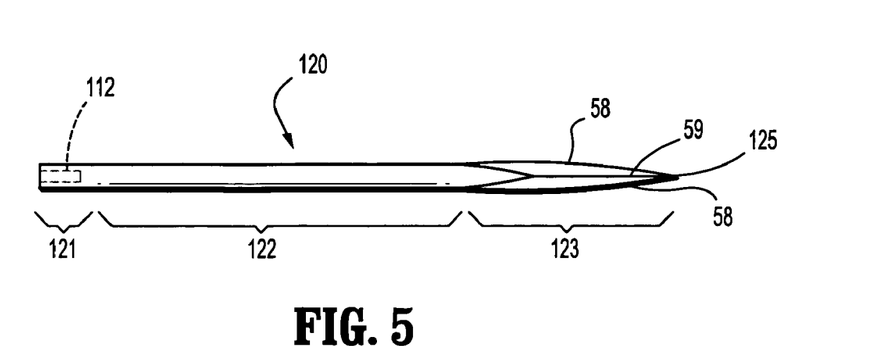
FIG. 5 is a view of the needle end formed in accordance with the present disclosure.

FIG. 5 illustrates the bayonet needle 120 formed in accordance with the above-described illustrative process. Needle 120 includes a suture attachment portion 121 at the proximal end of needle 120 that includes a bore 112 for receiving a suture. Needle 120 also includes body portion 122 having either a generally triangular or a generally trapezoidal cross-section, depending on whether the optional flat press operation 40 is performed. Needle 120 further includes distal end portion 123 containing pointed tip 125 and cutting edges 58, 59. The outer cutting edges 58 are formed along the line where upper punch 49 meets left and right dies 42, 44 of the bayonet prepoint pressing operation 20 and bayonet finish pressing operation 30 (as depicted in FIG. 3A). The central cutting edge 59 is formed along the line of intersection of the angled cuts 46 of the left and right dies 42, 44 of the bayonet form processes 20 and 30 (as depicted in FIG. 3A).

It will be understood that various modifications may be made to the embodiments disclosed herein. For example, the aforementioned grindless operation may be adapted to form other needle configurations besides the bayonet configuration disclosed, such as, for example, taper point needles, star-shaped needles and the like. These alternate designs may be achieved by appropriate alternate designs to the dies employed in the pressing operations. Therefore, the above description should not be construed as limiting, but merely as exemplifications of typical embodiments. Those skilled in the art will envision other modifications within the scope and spirit of the claims appended hereto.

What is claimed is:

1. A process for manufacturing a surgical needle comprising:
    pressing a needle blank to define a needle comprising a distal end and a body portion wherein flash material surrounds a portion of the distal end;
    orienting the needle vertically alone its longitudinal axis over an acid bath with the distal end pointed down; and
    immersing at least a portion of the needle in the acid bath according to a predetermined immersing sequence wherein the distal end is exposed to the acid bath under conditions sufficient to remove flash material from the distal end and wherein the body portion of the needle is exposed to the acid bath under conditions sufficient to provide a matte finish on at least a portion of the body portion of the needle.

2. The process according to claim 1 wherein the step of pressing includes positioning at least a portion of the distal end of the needle blank between three dies defining a triangular recess therein and engaging the at least a portion of the distal end of the needle blank with the die surfaces defining the triangular recess to impart a substantially triangularly-shape to the at least a portion of a distal end of the needle blank.

3. The process according to claim 2 wherein the step of pressing includes positioning at least a portion of the substantially triangularly-shaped distal end of the needle blank between two dies and a press defining a triangular recess therebetween and engaging the at least a portion of the substantially triangularly-shaped distal end of the needle blank with the die surfaces and the press to impart a generally tapered configuration to the at least a portion of the substantially triangularly-shaped distal end of the needle blank.

4. The process according to claim 2 wherein the step of pressing includes positioning at least a portion of the substantially triangularly-shaped distal end of the needle blank between an upper punch and a lower die and engaging the at least a portion of the substantially triangularly-shaped distal end of the needle blank with the upper punch and a lower die to impart a generally trapezoidal configuration to the at least a portion of the substantially triangularly-shaped distal end of the needle blank.

5. The process of claim 1 wherein the step of immersing comprises immersing the needle in composition containing an acid selected from the group consisting of phosphoric acid, sulfuric acid, glycolic acid, and combinations thereof.

6. The process of claim 1 wherein the acid bath is maintained at a temperature of from about 80° F. to about 200° F.

7. The process of claim 1 wherein the acid bath is maintained at a temperature of from about 90° F. to about 110° F.

8. The process of claim 1 wherein the needles are immersed in the acid bath for a total time of from about 60 seconds to about 500 seconds.

9. The process of claim 1 wherein further comprises applying a voltage to the needle of from up to 30 volts while the distal end of the needle is immersed in the acid bath.

10. A process for manufacturing a surgical needle, comprising the steps of:
- pressing a needle blank to define a needle comprising a distal end and a body portion wherein flash material surrounds a portion of the distal end;
- orienting the needle vertically along its longitudinal axis with its distal end down;
- immersing the needle in an acid bath according to a predetermined sequence wherein a tank holding the acid bath is raised so that the distal end of the needle enters the acid bath first and is exposed to the acid bath under conditions sufficient to remove flash material from the distal end and subsequently immersing the body portion of the needle into the acid bath such that the body portions of the needle is exposed to the acid bat under conditions sufficient to provide a matte finish on at least a portion of the body portion of the needle.

11. The process of claim 10 wherein the acid bath is maintained at a temperature of from about 80° F. to about 200° F.

12. The process of claim 10 wherein the acid bath is maintained at a temperature of from about 80° F. to about 200° F.

13. The process of claim 10 wherein the distal end of the needle is immersed in the acid bath for a period of time at least about twice as long as the period of time that the body portion of the needle is immersed in the acid bath.

14. The process of claim 10 wherein the distal end of the needle is immersed in the acid bath for a period of time about four times as Long as the period of time that the body portion of the needle is immersed in the acid bath.

15. The process of claim 10 wherein at least a portion of the distal end of the needle is subjected to a voltage greater than the voltage applied while at least a portion of the body portion of the needle is immersed in the acid bath.

16. The process of claim 10 wherein at least a portion of the distal end of the needle is subjected to a voltage at least about two times the voltage applied while at least a portion of the body of the needle is immersed in the acid bath.

17. A process for manufacturing a surgical needle, comprising the steps of:
- pressing a needle blank to define a needle comprising a distal end and a body portion wherein flash material surrounds a portion of the distal end;
- orienting the needle vertically along its longitudinal axis with its distal end down;
- immersing the needle in an acid bath according to a predetermined sequence wherein a tank holding the acid bath is raised so that at least a portion of the distal end of the needle enters the acid bath first and is exposed to the acid bath for a first period of time while being subjected to a first voltage; and
- subsequently immersing at least a portion of the body portion of the needle into the acid bath for a second period of time less than said first period of time and at a second voltage less than said first voltage.

18. A process as in claim 17 wherein the first period of time is at least about twice as long as the second period of time.

19. A process as in claim 17 wherein the first period of time is at least about four times as long as the second period of time.

20. A process as in claim 17 wherein the first voltage is at least about twice as much as the second voltage.

21. A process as in claim 17 further comprising immersing a second portion of the distal end of the needle into the acid bath for a third period of time while being subjected to a third voltage.

* * * * *